United States Patent [19]

Kronberg

[11] Patent Number: 5,251,490
[45] Date of Patent: Oct. 12, 1993

[54] ULTRASONIC FLUID FLOW MEASUREMENT METHOD AND APPARATUS

[76] Inventor: James W. Kronberg, 108 Independent Blvd., Aiken, S.C. 29801

[21] Appl. No.: 832,567

[22] Filed: Feb. 7, 1992

[51] Int. Cl.⁵ .............................................. G01F 1/66
[52] U.S. Cl. .................................. 73/861.25; 73/642
[58] Field of Search ........... 73/861.25, 861.26, 861.27, 73/861.28, 642, 644, 629, 865.5

[56] References Cited

U.S. PATENT DOCUMENTS

| | | | |
|---|---|---|---|
| 2,770,795 | 11/1956 | Peterson | 73/861.25 |
| 2,912,854 | 11/1959 | Schubring | 73/627 |
| 3,299,695 | 1/1967 | Dickinson | 73/627 |
| 3,741,014 | 6/1973 | Tamura | 73/194 A |
| 4,391,149 | 7/1983 | Herzl | 73/861.25 |
| 4,445,380 | 5/1984 | Kaminski | 73/642 |
| 4,523,122 | 6/1985 | Tone et al. | 73/644 |
| 4,608,507 | 8/1986 | Neubauer et al. | 310/335 |
| 4,852,575 | 8/1989 | Nikoonahad | 128/660.01 |
| 4,989,609 | 2/1991 | Smith et al. | 128/661.08 |
| 5,094,108 | 3/1992 | Kim et al. | 73/629 |

Primary Examiner—Richard E. Chilcot, Jr.
Assistant Examiner—Ronald L. Biegel
Attorney, Agent, or Firm—Harold M. Dixon; William R. Moser; Richard E. Constant

[57] ABSTRACT

An apparatus for measuring the flow of a fluid in a pipe using ultrasonic waves. The apparatus comprises an ultrasonic generator, a lens for focusing the sound energy produced by the generator, and means for directing the focused energy into the side of the pipe through an opening and in a direction close to parallel to the long axis of the pipe. A cone carries the sound energy to the lens from the generator. Depending on the choice of materials, there may be a quarter-wave, acoustic impedance matching section between the generator and the cone to reduce the reflections of energy at the cone boundary. The lens material has an acoustic impedance similar to that of the cone material but a different sonic velocity so that the lens can converge the sound waves in the fluid. A transition section between the lens and the fluid helps to couple the energy to the fluid and assures it is directed as close to parallel to the fluid flow direction as possible.

20 Claims, 1 Drawing Sheet

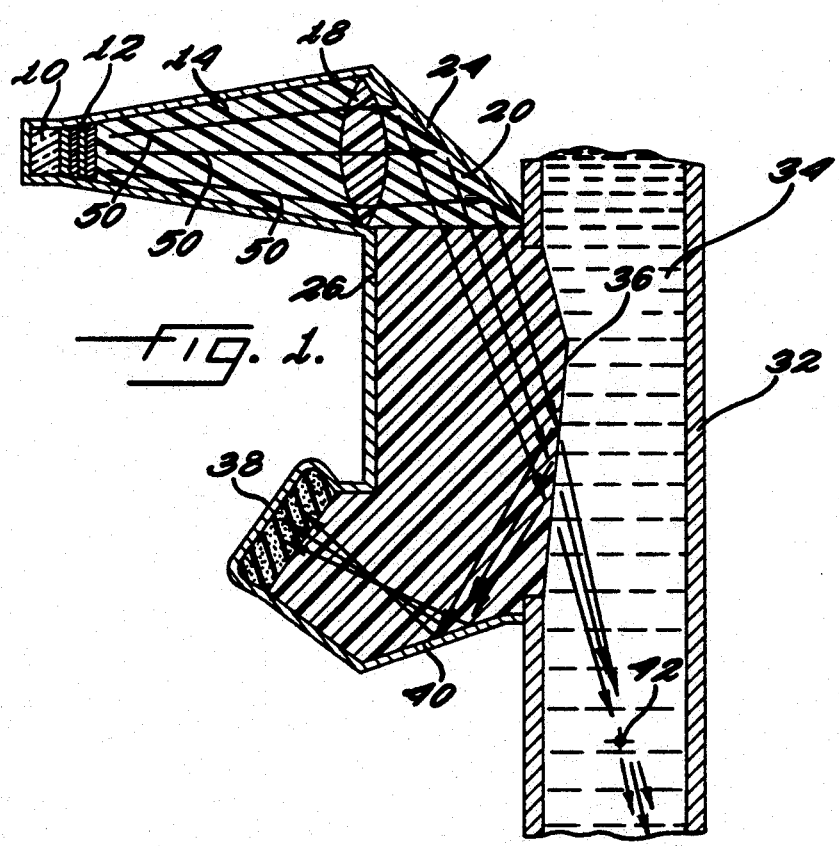
Fig. 1.
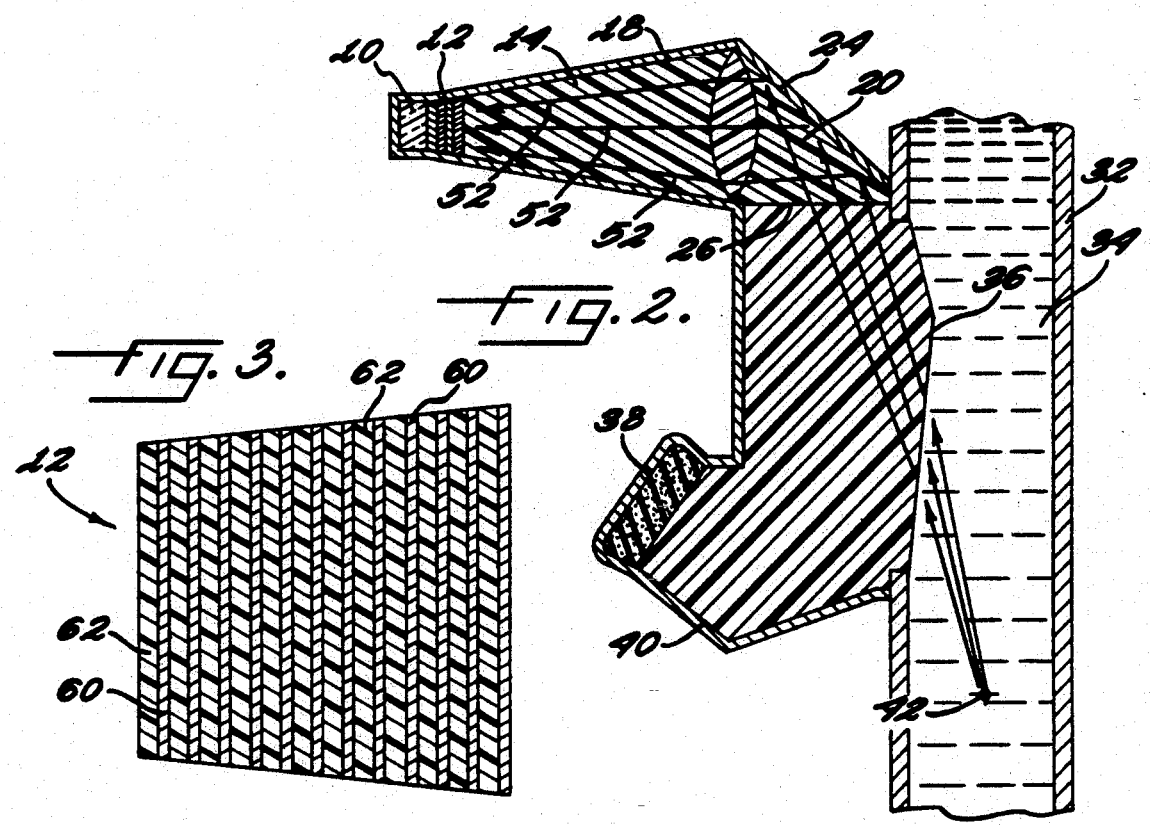
Fig. 2.
Fig. 3.

ULTRASONIC FLUID FLOW MEASUREMENT METHOD AND APPARATUS

The U.S. Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to measuring fluid flow. In particular, the present method relates to measuring fluid flow in vessels by ultrasonic means.

2. Discussion of Background

In industrial piping, chemical and nuclear reactors, and elsewhere, it is often necessary to measure the direction and speed of flow of a liquid, gas or slurry. Ideally, this should be accomplished without the need to intrude upon the process being measured. Probes extending into a process line or reactor will, of necessity, disturb the very flow patterns to be measured. Corrosive conditions, high temperatures or pressures, radioactivity, or a combination of these conditions within a reactor or other system may also place severe restrictions upon the materials from which a sensing probe may be constructed, and may also pose the danger of leakage at the point where the probe is inserted.

Instead of a material probe, any one of several forms of energy may be sent into the system; the subsequent behavior of this energy may reveal information about flow patterns. Most commonly, either ultrasonic waves or laser light are used. Inhomogeneities within the system, such as small bubbles or bits of suspended matter, reflect a small portion of the energy back to the radiation source or to a detector placed nearby. Doppler shifts in the reflected energy, showing up as changes in frequency or wavelength, reveal the velocity of motion of the reflecting objects, and hence (usually) of the bulk liquid; unshifted energy, reflected from stationary structural features, can be ignored.

Laser light has the advantage of being able to be precisely focused so that flow rates may be read in a relatively small volume, with minimal interference from the motion of reflecting particles in other parts of the vessel traversed by the beam. However, not all systems permit laser light to be used; some liquids are cloudy or strongly absorbing, and devices are needed to couple the energy efficiently into and out of the system.

Ultrasonic energy is more widely used, since it requires no window and is not so readily absorbed or scattered; ultrasonic transducers are simply attached to the walls of a vessel or to the surface of a pipe, with or without special fittings. At present, however, no ultrasonic flow-measuring systems seem to exist that have the "point-focus" capability of a laser; hence, ultrasonic measurements are typically average values for relatively large volumes of liquid. Such measurement suffices for laminar flow applications, such as with fluid moving slowly through a smooth walled pipe, but is of little value when flow is turbulent.

A means of focussing and controlling ultrasonic waves, permitting "point-focus" capability, would permit convenient and non-intrusive measurement of flow even under turbulent conditions without the need for installation of optical fibers or ports and regardless of the color or turbidity of the fluid under study.

SUMMARY OF THE INVENTION

According to its major aspects and broadly stated, the present invention is an apparatus for use in measuring the speed and direction of fluid flowing in a pipe. The apparatus comprises means for generating sound waves such as an ultrasonic transducer, a cone and lens for focusing said sound waves from the transducer, means for directing the focused sound waves through an opening in the pipe so that they are close to parallel to the long dimension of the pipe; and means for detecting any sound waves reflected by inhomogeneities within the fluid. Preferably there is also a means for absorbing any sound reflected at the boundary between the fluid and the directing means.

If the acoustic impedances between any two adjacent components of the apparatus differ, such as the cone and the transducer, matching sections preferably one-quarter wavelength long and having impedances logarithmically halfway between those of the two components are used to match impedances of the adjacent components, thereby limiting sonic reflections at the boundary therebetween.

Preferably the lens and the cone have similar acoustic impedances but different sonic velocities so that the lens can be designed to converge the sound waves. If the sonic velocity of the lens is lower, a bi-convex lens will converge the sound waves.

An important feature of the present invention is the focusing of the ultrasonic sound waves by a lens that has approximately the same acoustic impedance as the cone whence the sound waves are received but a different sonic velocity, preferably a lower sonic velocity. By having a lower sonic velocity, it is meant that the speed of sound in the material of the lens is lower than that in the material of the cone. Related to the feature of the focusing of sound waves by an acoustic lens is the choice of TEFLON as the lens material and polystyrene as the cone material. Both materials are readily available easy to work with and, being solids, hold their shapes without additional supporting structure.

Another important feature of the present invention is the use of an acoustic impedance matching section between the ultrasonic generator, preferably a piezoelectric crystal, and the cone when the acoustic impedance of the two do not match. The matching section should have an impedance between that of the generator and the cone, preferably logarithmically halfway between the two, to minimize reflections of sound energy at the cone boundary.

Yet another important feature of the present invention is the directing of the focused sound waves into the fluid through an opening in the side of the piping and at an angle nearly parallel to the direction of flow, a long the long axis of the pipe. By nearly parallel, it is meant that the sound energy follows a direction that has both a component parallel to the long axis of the pipe and a perpendicular component, and that the parallel component is greater than the perpendicular component.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a cross sectional view of an apparatus for measuring fluid flow according to a preferred embodiment of the present invention, the apparatus having arrows indicating the paths of transmitted sound;

FIG. 2 is a cross sectional view of the apparatus illustrated in FIG. 1 having arrows indicating the paths of reflected sound; and FIG. 3 is a detailed cross sectional view of the matching section according to an embodiment of the present invention.

DETAILED DESCRIPTION OF A PREFERRED EMBODIMENT

The invention is a device for generating an ultrasonic signal, coupling this signal into a body of flowing liquid in such a way that energy travels in a direction nearly parallel to the expected flow direction, typically parallel to the long axis of a pipe, and is brought to a focus within the liquid, then detecting any Doppler-shifted sound energy that is reflected back from inhomogeneities in the liquid at or near the focal point. The amplitude and direction of the Doppler-shifted sound energy indicates the speed and direction of flow at the focal point. The sensing device is designed so as to present only a smooth, non-obstructing surface to the flowing liquid.

This invention makes it possible to apply the "point focus" (meaning focusing sound energy on a very small volume) flow-sensing method, previously limited to laser systems, to ultrasonic flow measurement and hence to a variety of dark or turbid fluids not compatible with laser light.

Just as light may be focused by lenses made of transparent material (such as glass) that varies its speed, so may ultrasonic waves be focused by lenses made from materials in which the speed of sound varies. Although normally severe, the loss of energy through reflection at the boundaries of such objects can be mitigated by selection of materials having properly chosen acoustic impedances, either equal or progressing in evenly-spaced logarithmic steps from one material to the next. If such materials are also convenient to shape, fittings may be easily made which will permit focused ultrasonic energy to be sent to virtually any preselected small volume of a system under study and return information on fluid flow.

Sound velocity and acoustic impedance are tabulated in a number of handbooks. Typically, sound velocity is given in meters per second, and acoustic impedance in kilograms per square meter per second, indicating the mass of material traversed by a square meter wavefront in one second.

Materials having roughly equal acoustic impedance show very little energy loss by reflection when sound passes from one into the other. If the speed of sound differs from one such material to the other, refraction will occur without a corresponding degree of reflection. If a convex or concave body of one such material is enclosed by the other material, it will act as a lens, focusing sound waves passing through it.

For example, an acoustic lens could be formed by SAE 20 oil (light machine oil) surrounded by water, or vice-versa; the impedances of the two liquids are similar, but sound travels faster through oil than through water, so refraction would occur. The two liquids could be separated and held in shape by thin membranes of rubber or plastic, rigidly supported at the edges.

It should be noted that very different effects would appear depending on the relative placement of the two materials. A lens of water surrounded by oil would affect sound in the same way a glass lens affects light; a convex lens would focus the energy, while a concave lens would disperse it. This is true because sound travels more slowly in water than in oil, just as light travels more slowly in glass than in air. For an oil lens in water, the effect would be just the opposite: a convex lens would cause the energy to diverge, while a concave lens would focus it.

Similarly, lenses could be formed by suitably-shaped solid masses of polystyrene and TEFLON, of lead and zinc, or, with somewhat higher reflective losses, of copper and steel.

Transfer of energy from one medium to another will be inefficient, due to reflective losses, if the acoustic impedances of the two materials differ significantly. However, this problem may be largely overcome if a third material exists whose impedance is close to the geometric mean between those of the other two materials. This material is simply inserted between the others, causing the impedance to increase in two logarithmically-equal steps rather than in a single step. If no such material can be identified, materials that bracket the desired value can be combined: for example, by stacking alternating thin sheets of polyethylene and of lead or aluminum and orienting the stack perpendicularly to the direction of sound propagation, or by melting together zinc and copper to form brass.

The best matching takes place when the intermediate material has a thickness of one-quarter wavelength of the ultrasonic energy in that material. For example, the acoustic impedance of high-density polyethylene is roughly midway between those of polystyrene (or a fluorocarbon such as TEFLON) and water. For a typical frequency of 40 kilohertz, the wavelength in polyethylene is about 55 millimeters, so a quarter-wave matching layer would be about 14 millimeters thick, just over a half-inch. For higher frequencies, the quarter-wave thickness would be proportionately lower.

In the case of an ultrasonic transducer, matching must take place not only between the various transmissive materials used in the system, but also between the system and the transducer itself. Such a transducer is typically a specially-cut piece of piezoelectric crystalline material, such as PZT-5 (lead zirconate-titanate) or ADP (ammonium dihydrogen phosphate).

For a system using lenses of lead and zinc, a PZT-5 transducer may be used without matching, since the impedances of all three substances are virtually equal. For a system with lenses of water and oil, where the impedances are close but unequal, a fair match can be made with an ADP transducer using no matching section, but a much better match can be made by the following means.

While no tabulated pure substance has an impedance close to 4.1, the approximate value needed for a quarter-wave matching section between lead and zinc lenses this impedance can be attained by using a quarter-wave thick stack of alternating thin sheets of polyethylene and aluminum foil. The impedance of such a stack $Z_{stack}$ is given by:

$$Z_{stack} = Z_{al} \times T_{al} = Z_{p.e.} \times T_{p.e.}$$

in which $T_{al}$ and $T_{p.e.}$ are the time spent by the energy in traversing the aluminum and polyethylene, respectively, and $Z_{al}$ and $Z_{p.e.}$ are the impedances of aluminum and polyethylene, respectively. For a $Z_{stack}=4.1$ based on a stack of alternating sheets of aluminum and polyethylene, $Z_{al}$ will be 0.129 and $Z_{p.e.}$ will be 0.871. During one-fourth cycle at 40 KHz (6.25 microseconds), $T_{al}$ and $T_{p.e.}$ will be 0.81 and 5.44 microseconds, respectively, corresponding to material thicknesses of 5.2 and 12.0 millimeters, respectively. An effective quarter-wave matching layer can therefore be built up, for example, by alternating thirty-two layers of 38-gauge (0.159 mm) aluminum sheet and of 15-mil (0.381 mm) polyethylene.

Tightly-focused ultrasonic energy, suitable for point focus Doppler flow measurements, can be produced by mounting a transducer at the apex of a cone of a suitable material, leading to one or more acoustic lenses that are coupled on their distal sides to the vessel in which measurements are to be taken. All abrupt discontinuities in acoustic impedance should be cushioned by appropriate quarter-wave plates. Matching between the transducer and the cone may be accomplished by making the end portion of the cone itself a quarter-wave matching section. If desired, one or more discontinuities may be introduced deliberately as reflecting surfaces to steer the beam in a desired direction.

A transition section, machined or otherwise shaped to fit the surface contour of a pipe or vessel, and made from the same material or one of similar impedance, may be used to couple energy into (and out of) the equipment to be monitored. Unfortunately, large amounts of energy are likely to be lost at the interface between the vessel wall and the fluid inside, and the beam may be undesirably refracted as well; this is particularly true of metal vessels holding light fluids such as water, oil or gases.

In such a case, energy losses can be reduced and accuracy increased by mounting a plug of lower-impedance material perhaps ending in a quarter-wave matching sheet, through the side of the pipe or vessel or through a fitting attached to it, so as to contact the liquid directly.

TEFLON is particularly promising for applications of this sort, since it is chemically inert, remains solid and stable over a very wide temperature range, is unlikely to be fouled or abraded by impurities in the stream, and has an acoustic impedance and transmission speed not greatly different from those of water and most common organic liquids. Furthermore, advantage can be taken of the fact that, since the speed of sound is actually less in TEFLON than in these other liquids, energy passing from the TEFLON to the liquid will be refracted into a direction more nearly parallel to their interface.

Referring now to FIGS. 1 and 2, small piezo-electric transducer 10 made from ammonium dihydrogen phosphate (ADP) and optimized for use at 100 kiloHertz, is coupled to a quarter-wave transition section 12 that is built up from twelve layers 60, 62, each of 38-gauge aluminum and 15-mil polyethylene sheeting, respectively, layers 60, 62 of the two materials alternating and oriented parallel to the energy-emitting surface of the transducer, as shown in FIG. 3.

The distal side of transition section 12 is coupled to the truncated tip of a polystyrene cone 14, whose base 16 is hollowed to fit one surface of a bi-convex TEFLON lens 18. The dimensions of lens 18 are chosen so as to refract the diverging sound energy from transducer 10, transmitted through cone 14, into a slightly converging pattern, as detailed below.

Abutting lens 18 is a TEFLON block 20 taking the form of a prism with one face 22 hollowed to fit the surface of lens 18, and faces 24, 26 flat and suitably angled to direct sound through total internal reflection into a second TEFLON block 30. Face 24 forms an approximately fifty-degree angle with face 22, while faces 22 and 26 are approximately perpendicular, as shown in FIGS. 1 and 2. Alternatively, blocks 20 and 30 may be formed from a single block of TEFLON, or such a body may be made up from pieces divided in a way different from that shown in the figure. Block 30 penetrates a wall of pipe 32 containing a liquid 34 whose velocity is to be measured. Surface 36 of block 30 is in direct contact with the liquid. Pipe 32 has longitudinal axis A, parallel to the direction of flow of liquid 34. Surface 36 may take any form, flat or curved, as may be found to yield the best balance of sound energy direction and focusing with minimal disturbance of the liquid stream, such as a slightly raised form, analogous to the upper curve of an aircraft wing, as illustrated. Note that the greater portion of surface 36 is flat and angled slightly inwardly in relation to the pipe surface.

Mounted on the end of block 30, opposite prism 20, is a pad 38 made of sound-absorbing material such as acoustical foam. This material needs to be chosen so as to have an acoustical impedance close to that of TEFLON, so that essentially all of the energy striking it penetrates and is dissipated as heat. Alternatively, an optional flat, polished face 40 may be located at the end of block 30, as shown, to redirect the energy; pad 38 may then be located elsewhere, as convenient.

In operation, sound energy (represented in the following diagram by arrows 50) in emitted by transducer 10, is coupled into cone 14 by quarter-wave section 12, and propagates, steadily diverging, down the length of cone 14, which widens with length to accommodate the divergence. Passing through surface 16, the energy enters lens 18. Since the speed of sound is less in TEFLON than in polystyrene, refraction occurs and the diverging wavefronts are curved so as to converge slowly during subsequent travel.

Leaving lens 18 through surface 22, the energy passes into prism 20 and is reflected from polished surface 24, with a roughly eighty-degree change in direction. Passing through surface 26 into block 30, sound energy strikes surface 36, which is in contact with liquid 34. Surfaces 24 and 36 are mutually oriented so that the energy strikes surface 36 at a shallow angle of approximately twenty degrees, to longitudinal axis A of pipe 32, in a direction subparallel to axis A. Thus, sound energy entering fluid 34 has velocity components parallel and perpendicular to axis A, with the parallel component greater than the perpendicular component.

Because the energy strikes surface 36 at such a shallow angle, some of it is reflected back into block 30 and continues onward, striking surface 40 and undergoing reflection to enter pad 38, which absorbs it. The remainder of the energy passes through surface 36 and enters liquid 34, undergoing refraction so that its path in the liquid is nearly parallel to the length of pipe 32. Because of the convergence introduced by lens 18, the energy is focused at a point 42 close to the central axis of the pipe.

Were liquid 34 perfectly homogeneous, all of the sound energy passing into it through surface 36 would continue on through it until it struck, and was reflected by, stationary portions of pipe 32 or adjacent structures; a small portion of this energy might then return through surface 36, but because reflected energy had come from structures stationary with respect to surface 36, no Doppler shifting would occur and the reflected energy would have the same frequency, 100 kiloHertz, as that emitted by the transducer.

In a normal liquid stream, however, a portion of the energy would be reflected from inhomogeneities in the stream, such as bubbles, suspended solid particles, or droplets of a minority liquid phase. Because these would travel with the stream, energy reflected from them would be Doppler-shifted by an amount proportional to the speed of motion. Reflection would be strongest near focal point 42.

Reflected, Doppler-shifted sound energy, indicated by lines 52 would return through surface 36 and through all of the aforementioned structures in reverse order, retracing the path of the energy emitted by transducer 10, until the reflected and shifted energy returned to the transducer.

Relatively simple electronic means, taking any one of several commonly used forms, would be used to drive transducer 10 intermittently at 100 kiloHertz and to monitor its output (caused by reconversion of the reflected energy from acoustic to electrical form) for frequencies slightly shifted from the driving frequency. Unshifted reflections would be ignored. The direction and magnitude of any detected frequency shift would indicate the direction and speed of motion of liquid in the pipe.

It will be apparent to those skilled in the art that many changes and substitutions can be made to the preferred embodiment herein described without departing from the spirit and scope of the present invention as defined by the appended claims.

What is claimed is:

1. Apparatus for use in measuring the speed and direction of fluid flowing in a pipe, said pipe having a longitudinal axis and an opening, said apparatus comprising:
    means for generating sound waves;
    means for focusing said sound waves; including a cone having a proximal end and a distal end, said proximal end facing said generating means, said cone receiving said sound waves from said generating means at said proximal end and guiding said sound waves to said distal end;
    means for directing said focused sound waves through said opening at an angle subparallel to said longitudinal axis, said sound waves propagating in said pipe with a velocity having a component parallel to said longitudinal axis and a component perpendicular to said longitudinal axis, said parallel component being greater than said perpendicular component; and
    means for detecting sound waves reflected by inhomogeneities within said fluid.

2. The apparatus as recited in claim 1, wherein said apparatus further comprises means for matching the acoustic impedance of said generating means to the acoustic impedance of said directing means.

3. The apparatus as recited in claim 1, further comprising an acoustic impedance matching plate positioned between said generating means and said focusing means, said matching plate having an acoustic impedance between the acoustic impedance of said generating means and the acoustic impedance of said directing means.

4. The apparatus as recited in claim 1, wherein said focusing means further comprises:
    a lens receiving said sound waves from said distal end of said cone and adapted for converging said sound waves, said cone and said lens having different sonic velocities.

5. The apparatus as recited in claim 1, wherein said focusing means further comprises:
    a biconvex lens receiving said sound waves from said distal end of said cone and adapted for converging said sound waves, said lens having a lower sonic velocity than said cone.

6. The apparatus as recited in claim 1, wherein said focusing means further comprises:
    a lens receiving said sound waves from said distal end of said cone and adapted for converging said sound waves, said cone and said lens having approximately equal acoustic impedances but different sonic velocities.

7. The apparatus as recited in claim 1, wherein at least a portion of said sound waves are reflected at the boundary of said fluid at said opening, further comprising means for absorbing said reflected sound waves.

8. The apparatus as recited in claim 1, wherein said sound generating means is an ultrasonic transducer.

9. The apparatus as recited in claim 1, wherein said sound generating means further comprises a piezoelectric crystal.

10. Apparatus for use in measuring the speed and direction of fluid flowing in a pipe, said pipe having a longitudinal axis and an opening, said apparatus comprising:
    means for generating ultrasonic sound waves;
    a cone having a proximal end and a distal end, said proximal end facing said generating means, said cone receiving said sound waves from said generating means at said proximal end and guiding said sound waves to said distal end;
    a lens for receiving said sound waves from said distal end of said cone and adapted for converging said sound waves, said cone and said lens having different sonic velocities;
    means for directing said converged sound waves through said opening at an angle subparallel to said longitudinal axis, said sound waves propagating in said pipe with a velocity having a component parallel to said longitudinal axis and a component perpendicular to said longitudinal axis, said parallel component being greater than said perpendicular component; and
    means for detecting sound waves reflected by inhomogeneities within said fluid.

11. The apparatus as recited in claim 10, wherein at least a portion of said sound waves are reflected at the boundary of said fluid at said opening, further comprising means for absorbing said reflected sound waves.

12. The apparatus as recited in claim 10, wherein said generating means further comprises a piezoelectric crystal.

13. The apparatus as recited in claim 10, further comprising a matching section positioned between said generating means and said cone and having an acoustic impedance between the impedance of said generating means and said cone.

14. The apparatus as recited in claim 10, further comprising a matching section positioned between said generating means and said cone and having an acoustic impedance logarithmically halfway between said generating means and said cone.

15. The apparatus as recited in claim 10, wherein said cone and said lens have approximately equal acoustic impedances but different sonic velocities.

16. The apparatus as recited in claim 10, wherein said lens is a biconvex lens having a lower sonic velocity than said cone.

17. Apparatus for use in measuring the speed and direction of fluid flowing in a pipe, said pipe having a longitudinal axis and an opening, said apparatus comprising:
    an ultrasonic transducer;
    a cone having a proximal end and a distal end, said proximal end facing said generating means, said cone receiving said sound waves from said generating means at said proximal end and guiding said sound waves to said distal end;
    means for matching the impedances of said transducer and said cone;
    a lens for receiving said sound waves from said distal end of said cone and adapted for converging said sound waves, said cone and said lens having different sonic velocities;
    means for directing said converged sound waves through said opening at an angle subparallel to said longitudinal axis, said sound waves propagating in said pipe with a velocity having a component parallel to said longitudinal axis and a component perpendicular to said longitudinal axis, said parallel component being greater than said perpendicular component; and
    means for detecting sound waves reflected by inhomogeneities within said fluid.

18. The apparatus as recited in claim 17, wherein said matching means is a matching section positioned between said transducer and said cone and having an acoustic impedance logarithmically halfway between said transducer and said cone.

19. The apparatus as recited in claim 17, wherein said matching means further comprises:
    a plurality of first layers, each of said first layers having a first acoustic impedance; and
    a plurality of second layers, said second layers alternating with said first layers, each of said second layers having a second acoustic impedance different from said first acoustic impedance.

20. The apparatus as recited in claim 17, wherein said lens is a biconvex lens having a sonic velocity approximately equal to that of said cone.

* * * * *